United States Patent
Kim et al.

(10) Patent No.: US 11,003,251 B2
(45) Date of Patent: May 11, 2021

(54) MODELING METHOD OF TACTILITY USING NERVE SPIKE PATTERN, TACTILITY MODEL AND MANUFACTURING METHOD OF TACTILITY USING NERVE SPIKE PATTERN

(71) Applicants: UNIST(ULSAN NATIONAL INSTITUTE OF SCIENCE AND TECHNOLOGY), Ulsan (KR); IUCF-HYU (INDUSTRY-UNIVERSITY COOPERATION FOUNDATION HANYANG UNIVERSITY), Seoul (KR)

(72) Inventors: Sung Phil Kim, Ulsan (KR); Ji Sung Park, Ulsan (KR); Dong Pyo Jang, Seongnam-si (KR); Sung Jun Jung, Suwon-si (KR)

(73) Assignees: UNIST (ULSAN NATIONAL INSTITUTE OF SCIENCE AND TECHNOLOGY), Ulsan (KR); IUCF-HYU (INDUSTRY-UNIVERSITY COOPERATION FOUNDATION HANYANG UNIVERSITY), Seoul (KR)

(*) Notice: Subject to any disclaimer, the term of this patent is extended or adjusted under 35 U.S.C. 154(b) by 41 days.

(21) Appl. No.: 16/706,614

(22) Filed: Dec. 6, 2019

(65) Prior Publication Data
US 2020/0110467 A1  Apr. 9, 2020

Related U.S. Application Data

(63) Continuation of application No. PCT/KR2018/006414, filed on Jun. 5, 2018.

(30) Foreign Application Priority Data

Jun. 7, 2017 (KR) .................. 10-2017-0070806

(51) Int. Cl.
G06F 3/01 (2006.01)
A61N 1/04 (2006.01)

(52) U.S. Cl.
CPC .......... *G06F 3/016* (2013.01); *A61N 1/0456* (2013.01); *G06F 3/015* (2013.01)

(58) Field of Classification Search
CPC ........ G06F 3/016; G06F 3/015; A61N 1/0456
(Continued)

(56) References Cited

U.S. PATENT DOCUMENTS 10,166,394 B1 * 1/2019 Hoffmann ............ A61B 5/4836
10,627,914 B2 * 4/2020 Ang ........................ G06F 3/167

FOREIGN PATENT DOCUMENTS

KR          10-0626683 B1    9/2006
KR    10-2009-0014321 A      2/2009
(Continued)

OTHER PUBLICATIONS

International Search Report issued in PCT/JP2018/006414; dated Sep. 18, 2018.
(Continued)

*Primary Examiner* — Eric Blount
(74) *Attorney, Agent, or Firm* — Studebaker & Brackett PC

(57) ABSTRACT

The present invention relates to a method of modeling a tactile sensation using a nerve spike pattern, a tactile sensation model, and a method of generating a tactile sensation using a nerve spike pattern and may include generating a nerve spike pattern by sequentially arranging action potential spike time points of a nerve responding to a specific
(Continued)

pressure and modeling a pressure sensation for the pressure on the basis of the generated nerve spike pattern. According to the present invention, by checking how tactile sensation information is reflected in a nerve spike pattern, it is possible to provide a method capable of modeling various tactile sensations using the nerve spike pattern.

25 Claims, 16 Drawing Sheets

(58) Field of Classification Search
USPC .......................................... 340/407.1, 407.2
See application file for complete search history.

(56) References Cited

FOREIGN PATENT DOCUMENTS

| KR | 10-2012-0047493 A | 5/2012 |
|----|-------------------|--------|
| KR | 10-2015-0099510 A | 8/2015 |
| KR | 10-2016-0082987 A | 7/2016 |
| KR | 10-2016-0084401 A | 7/2016 |

OTHER PUBLICATIONS

Pereira J. C., Jr., Alves R. C. (2011). The labelled-lines principle of the somatosensory physiology might explain the phantom limb phenomenon. Med. Hypotheses 77, 853-856. 10.1016/j.mehy.2011.07.054.

* cited by examiner

Fig. 4C

| PRESSURE INTENSITY(mN) | 0.1 | 1 | 10 | 50 | 100 | 300 |
|---|---|---|---|---|---|---|
| SA1 | −15.39±1.17 | −12.98±1.06 | −17.05±0.54 | −16.63±0.41 | −15.54±0.49 | −14.03±0.48 |
| SA2 | −10.56 | −11.67 | −14.91 | −14.39 | −13.71 | −15.96 |

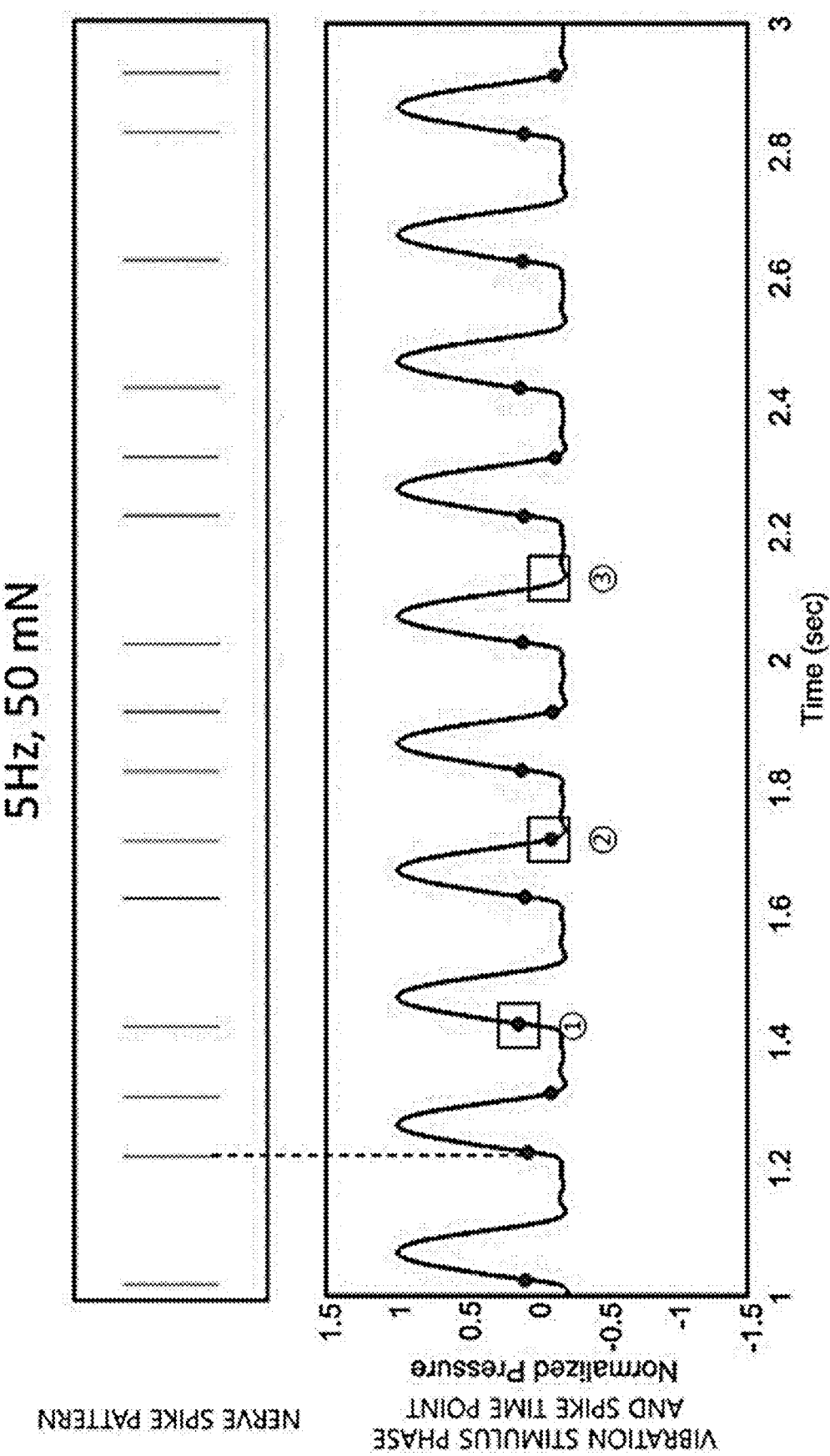

Fig. 10A

Phase (PROBABILITY)                                                                 Phase Unit : radian

| STIMULUS INTENSITY / FREQUENCY | 10 mN | 50 mN | 100 mN | 200 mN |
|---|---|---|---|---|
| 5 Hz | 4.48 (0.74) | 1.62 (0.46)<br>5.00 (0.84) | 0.68 (0.82)<br>3.96 (1.00)<br>4.59 (0.32) | 0.78 (0.48)<br>0.86 (0.54)<br>1.34 (0.24)<br>1.67 (1.00)<br>4.10 (1.00)<br>4.21 (0.04)<br>4.28 (0.94)<br>4.40 (0.66)<br>4.94 (1.00) |
| 10 Hz | 4.83 (0.37) | 4.32 (0.14)<br>4.52 (0.89)<br>5.60 (0.01) | 0.37 (0.25)<br>0.66 (0.55)<br>3.87 (0.89)<br>4.06 (0.42)<br>5.14 (0.04) | 0.38 (0.27)<br>0.72 (0.49)<br>3.62 (0.85)<br>3.93 (0.12)<br>4.74 (0.81) |
| 15 Hz | 4.54 (0.09) | 3.80 (0.01)<br>4.33 (1.00) | N/A | 3.23 (0.01)<br>3.48 (0.01)<br>3.74 (0.01)<br>4.08 (0.25)<br>4.37 (0.77)<br>5.58 (0.07) |
| 20 Hz | 1.15 (0.02)<br>3.19 (0.01)<br>3.87 (1.00)<br>5.04 (0.10) | 0.91 (0.08)<br>2.99 (0.01)<br>3.42 (0.06)<br>3.70 (0.99)<br>4.09 (0.83) | 1.08 (0.78)<br>2.48 (0.02)<br>3.56 (1.00)<br>4.22 (0.98)<br>5.14 (1.00) | N/A |

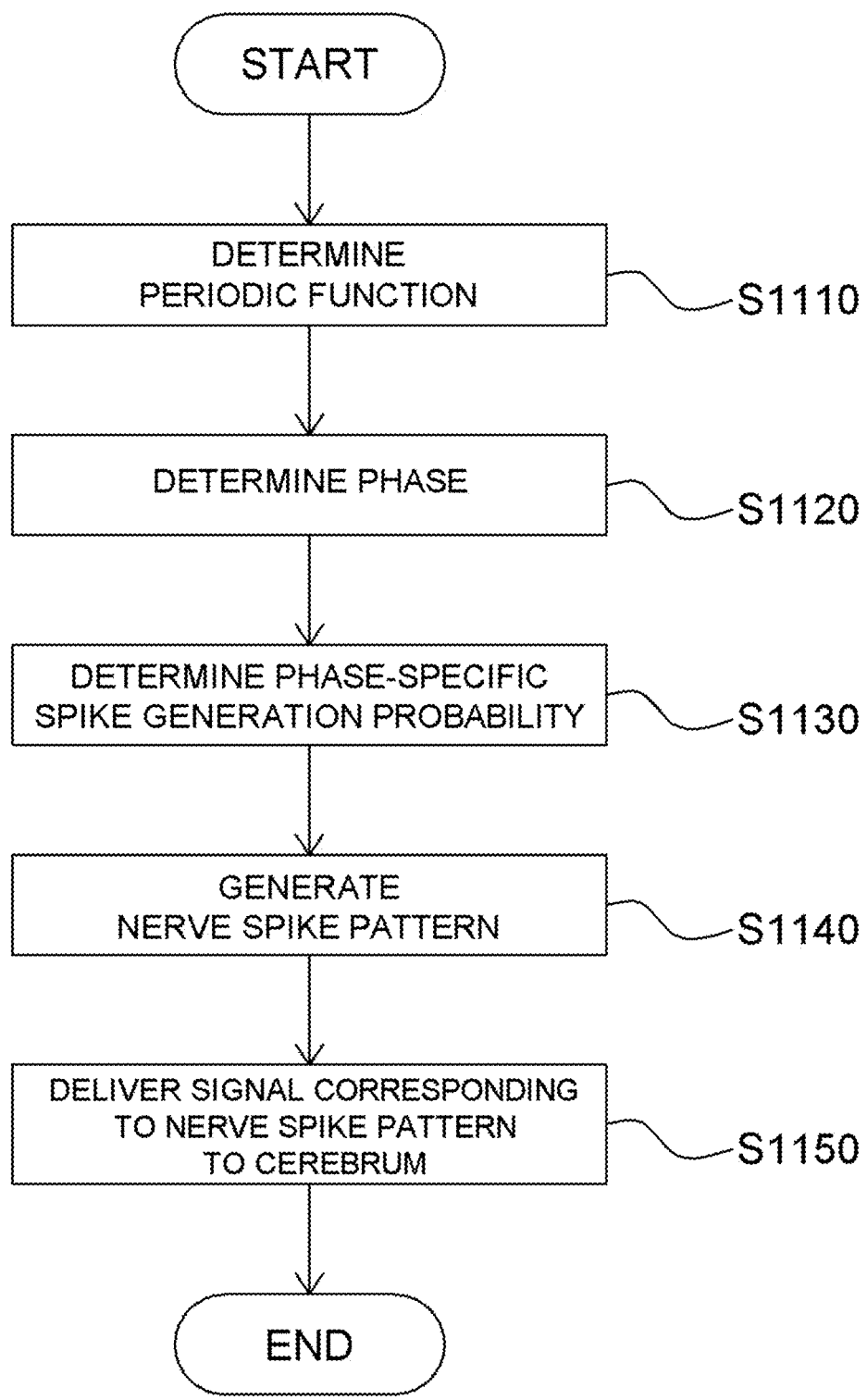

MODELING METHOD OF TACTILITY USING NERVE SPIKE PATTERN, TACTILITY MODEL AND MANUFACTURING METHOD OF TACTILITY USING NERVE SPIKE PATTERN

CROSS-REFERENCE TO RELATED APPLICATIONS

The present application is a continuation of International Patent Application No. PCT/KR2018/006414, filed Jun. 5, 2018, which is based upon and claims the benefit of priority to Korean Patent Application No. 10-2017-0070806, filed on Jun. 7, 2017. The disclosures of the above-listed applications are hereby incorporated by reference herein in their entirety.

TECHNICAL FIELD

The present invention relates to a method of modeling a tactile sensation using a nerve spike pattern, a tactile sensation model, and a method of generating a tactile sensation using a nerve spike pattern, and more particularly, to a method of modeling tactile sensation using a nerve spike pattern, a tactile sensation model, and a method of generating a tactile sensation using a nerve spike pattern in which tactile sensations caused by various stimuli may be modeled using the nerve spike pattern and in which a tactile sensation may be generated on the basis of the nerve spike pattern.

BACKGROUND ART

Virtual reality means any specific environment, situation or technology itself that is similar to reality but is not real and that is created by artificial technology using a computer or the like. Created virtual situations, environments, or the like stimulate the five senses of a user and enables spatial and visual experiences similar to reality.

In relation to the implementation of virtual reality, research and development have been actively conducted on technologies and output equipments capable of directly applying a physical impact to a user in a virtual space and implementing a tactile sensation in virtual reality such that the grip of an object, the temperature of an object, and the like can be felt. For example, a virtual reality-based haptic system capable of providing physical simulation by integrally controlling a three-dimensional (3D) haptic device and a 3D image display device with a computer has been disclosed (Patent Document 1 (Korean Patent Publication No. 10-2009-0014321)).

Thus, along with an increasing interest in tactile implementation and an increase in the interest and importance of related technologies, haptic devices are used in various fields. However, little is known about the neuroscientific mechanism of a tactile sensation compared to other sensations such as a visual sensation.

Until now, the transmission mechanism of a tactile sensation has been understood based on the labelled-line theory in which tactile sensation information is classified by one-to-one neural response mapping between stimuli and peripheral nerve receptors [Non-patent document 1 (Pereira J. C., Jr., Alves R. C. (2011). The labelled-lines principle of the somatosensory physiology might explain the phantom limb phenomenon. Med. Hypotheses 77, 853-856. 10.1016/j.mehy.2011.07.054.)]. However, it has never been clearly known how the spike pattern of peripheral nerves reflects, i.e., encodes tactile sensation information.

DISCLOSURE

Technical Problem

The present invention is designed to solve the above problems and is directed to providing a method capable of modeling various tactile sensations using a nerve spike pattern by checking how tactile sensation information is reflected in the nerve spike pattern.

The present invention is also directed to providing source technology capable of creating a tactile sensation map for various tactile sensations by allowing a tactile sensation model having information regarding the various tactile sensations to be modeled.

The present invention is also directed to providing a method capable of implementing a tactile sensation in virtual reality or the like by allowing a nerve spike pattern corresponding to a tactile sensation desired to be generated on the basis of a tactile sensation model.

The objects of the present invention are not limited to the above-mentioned objects, and other objects that are not mentioned will be clearly understood from the following description.

Technical Solution

According to an embodiment of the present invention, a method of modeling a tactile sensation using a nerve spike pattern may include generating a nerve spike pattern by sequentially arranging action potential spike time points of a nerve responding to a specific pressure; and modeling a pressure sensation for the pressure on the basis of the generated nerve spike pattern.

The modeling may include measuring the total number N of generated spikes and inter spike intervals (ISIs) between spike time points of the spikes on the basis of the generated nerve spike pattern; and modeling the pressure sensation through the measured total number of spikes and the measured ISIs between the spike time points.

The measured ISIs may be time-varying, and the measuring may include functionalizing a change in the ISIs with time using an ISI measured at a specific time.

A function obtained through the functionalizing may be $y=ax^5+b$, where x indicates time and y indicates ISI between spike time points, and the functionalizing may include computing a and b of the function according to x and y.

The functionalizing may be performed separately for a plurality of time intervals obtained through division.

The computing may be performed separately for a plurality of time intervals obtained through division.

After the modeling of the pressure sensation for the specific pressure, the generating and the modeling may be repeatedly performed under pressures different from the specific pressure.

According to another embodiment of the present invention, a method of modeling a tactile sensation using a nerve spike pattern may include generating a nerve spike pattern by sequentially arranging action potential spike time points of a nerve responding to a specific vibration stimulus; and modeling a vibration sensation for the vibration stimulus on the basis of the generated nerve spike pattern.

The modeling may include measuring phases of the vibration stimulus where spikes are generated in the generated nerve spike pattern; and calculating spike generation probabilities for the measured phases.

The measuring may include measuring the phases through Hilbert transform.

The calculating may include equally dividing a phase interval ranging from 0 to $2\pi$ into a plurality of phase intervals; and calculating the probability that each of the measured phases will belong to any one of the plurality of phase intervals.

The calculating may include counting the number of the measured phases belonging to each of the plurality of phase intervals to calculate a spike generation probability for each of the plurality of phase intervals.

After the modeling of the vibration sensation for the specific vibration stimulus, the generating and the modeling may be repeatedly performed under vibration stimuli different from the specific vibration stimulus.

According to another embodiment of the present invention, a tactile sensation model may be obtained through modeling by the method of modeling a tactile sensation using a nerve spike pattern.

According to another embodiment of the present invention, a method of generating a tactile sensation using a nerve spike pattern may include generating a nerve spike pattern corresponding to a specific pressure sensation in a pressure sensation model.

The method may further include delivering a signal corresponding to the generated nerve spike pattern to a cerebrum.

The generating may include determining the total number of spikes of the nerve spike pattern and inter spike intervals (ISIs) between spike time points of the spikes on the basis of the tactile sensation model; and arranging a number of spikes equal to the determined total number of spikes to be spaced the determined ISI apart from one another.

In the determining, the ISIs may be determined by a probability distribution having a preset mean and variance, and the mean may be a time interval value corresponding to a specific time in the tactile sensation model.

The probability distribution may be Poisson distribution or Gamma distribution.

According to another embodiment of the present invention, a method of generating a tactile sensation using a nerve spike pattern may include generating a nerve spike pattern corresponding to a specific vibration sensation in a vibration sensation model.

The method may further include delivering a signal corresponding to the generated nerve spike pattern to a cerebrum.

The generating may include determining a periodic function corresponding to the specific vibration sensation; and generating the nerve spike pattern on the basis of the determined periodic function and the tactile sensation model.

The generating may include determining phases of the periodic function corresponding to spikes of the nerve spike pattern on the basis of the tactile sensation model; determining spike generation probabilities for the determined phases on the basis of the tactile sensation model; and generating the nerve spike pattern on the basis of the determined phases and the determined spike generation probabilities.

The generating may include arranging the spikes according to the spike generation probabilities determined to correspond to the determined phases.

Specific details for achieving the above objects will be apparent with reference to the embodiments to be described below in detail with the accompanying drawings.

The present invention may, however, be embodied in different forms and should not be construed as limited to the embodiments set forth herein. Rather, these embodiments are provided so that this disclosure will be thorough and complete and will fully convey the scope of the present invention to those skilled in the art.

Advantageous Effects

According to the present invention, by checking how tactile sensation information is reflected in a nerve spike pattern, it is possible to more clearly understand a neuroscientific mechanism of a tactile sensation.

Also, a tactile sensation map for various tactile sensations may be created, and thus it is possible to implement a tactile sensation in virtual reality by using the tactile sensation map.

DESCRIPTION OF DRAWINGS

FIGS. 4A to 4C show graphs and tables showing spike model parameters of a generated pressure sensation model according to pressure intensity according to an embodiment of the present invention.

FIGS. 9A and 9B are diagrams showing an example of a nerve spike pattern for a vibration stimulus.

FIGS. 10A and 10B are diagrams showing a phase of a vibration stimulus where a spike is generated and a phase-specific spike generation probability.

FIG. 11 is a flowchart showing a method of generating a vibration sensation according to another embodiment of the present invention.

BEST MODES

Since the present invention may be variously modified and have several exemplary embodiments, specific exemplary embodiments will be shown in the accompanying drawings and described in detail.

Various features of the present invention disclosed in the claims may be better understood in view of the drawings and the detailed description. Apparatuses, methods, manufacturing methods, and various embodiments disclosed herein are provided for the purpose of illustration. The disclosed structural and functional features are intended to enable those skilled in the art to specifically practice various embodiments, and are not intended to limit the scope of the invention. The disclosed terms and sentences are intended to explain various features of the disclosed invention in an easy-to-understand manner and are not intended to limit the scope of the invention.

In the following description of the present invention, detailed descriptions of related well-known techniques will be omitted if it is determined that the detailed descriptions may unnecessarily obscure the subject matter of the present invention.

A method of modeling a tactile sensation using a nerve spike pattern, a tactile sensation model, and a method of generating a tactile sensation using a nerve spike pattern will be described below with reference to the accompanying drawings. The tactile sensation may be a pressure sensation or a vibration sensation.

First, a method of modeling a pressure sensation using a nerve spike pattern, a pressure sensation model, and a method of generating a pressure sensation according to an embodiment of the present invention will be described below.

Figure 1:
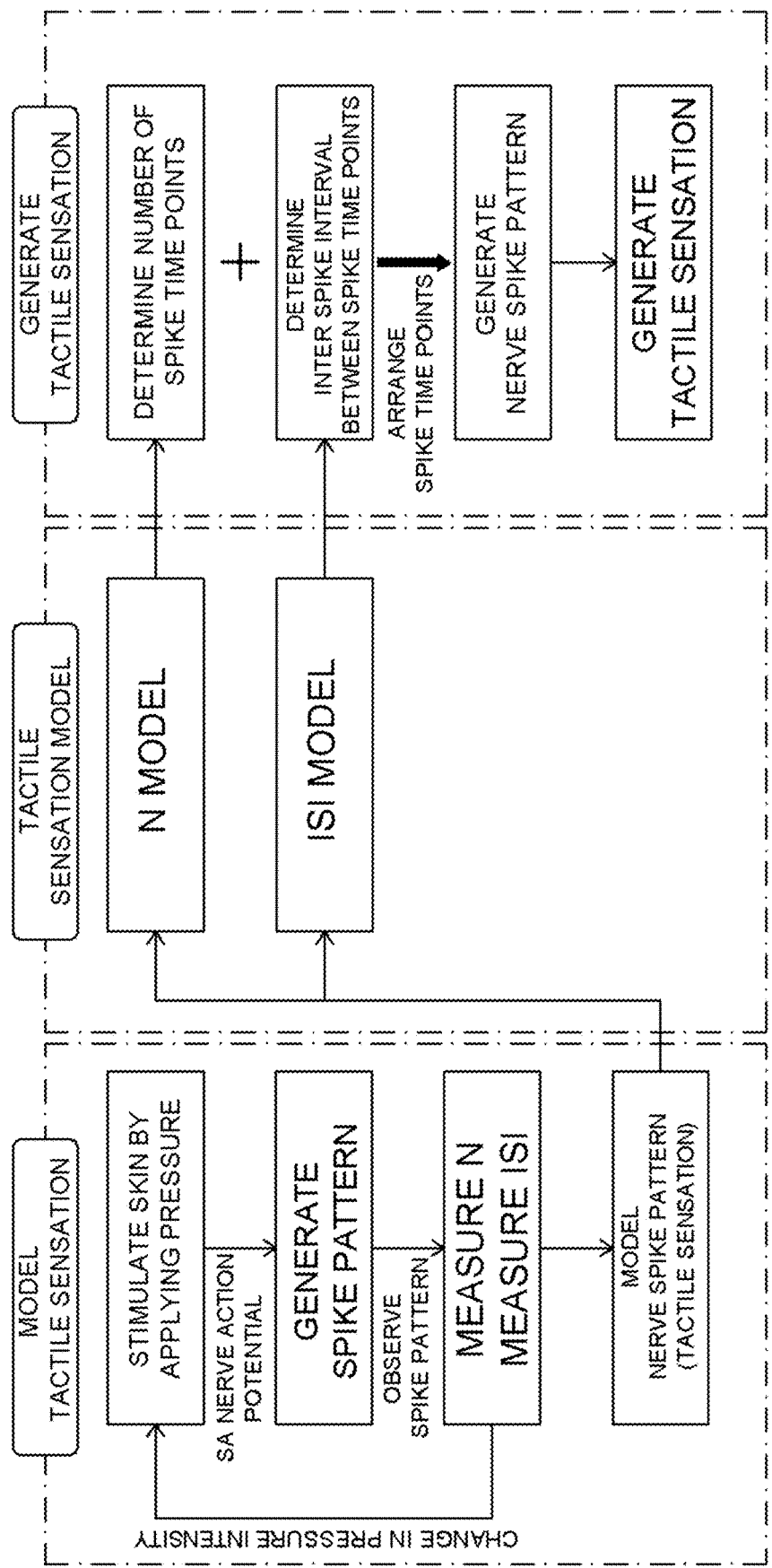
FIG. 1 is a flowchart showing a method of modeling a pressure sensation and a method of generating a pressure sensation according to an embodiment of the present invention.
Figure 2:
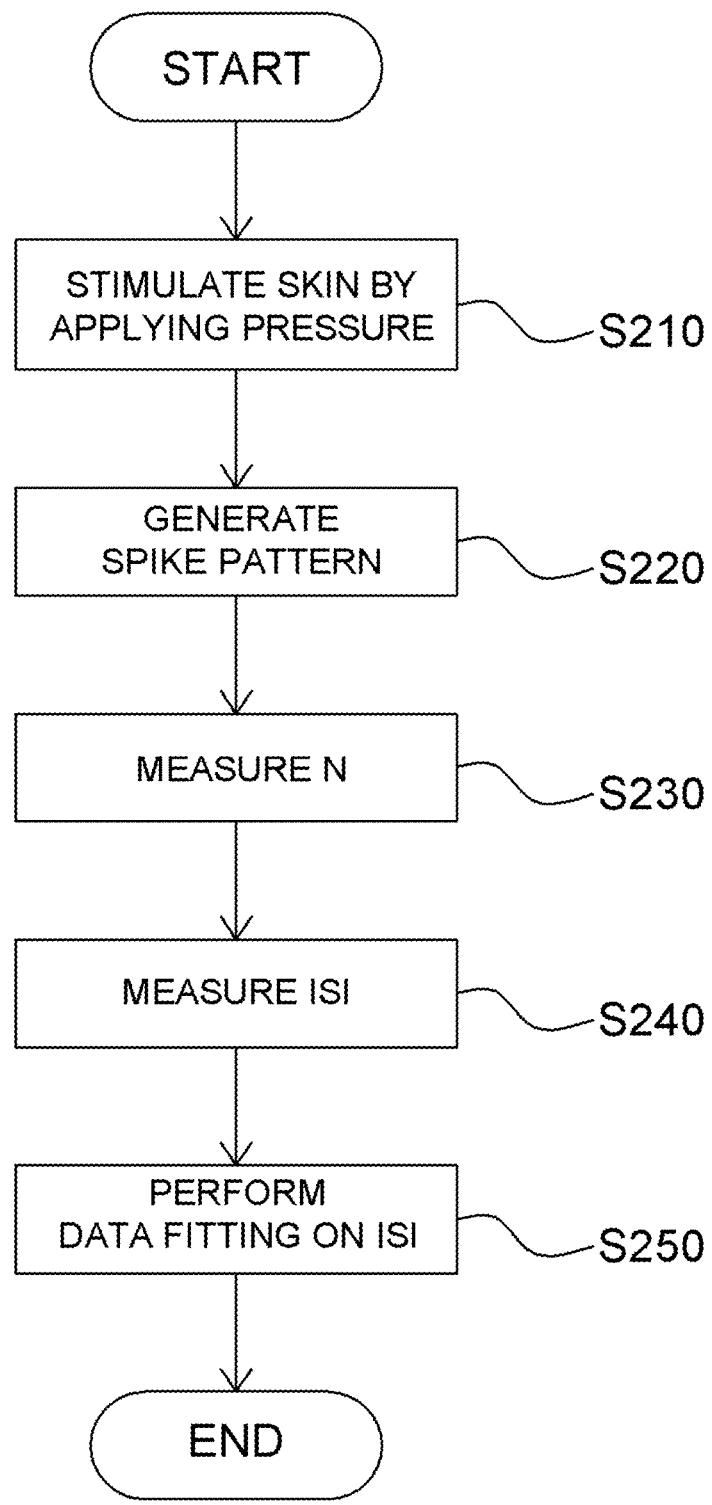
FIG. 2 is a flowchart showing a method of modeling a pressure sensation according to an embodiment of the present invention.
Figure 3:
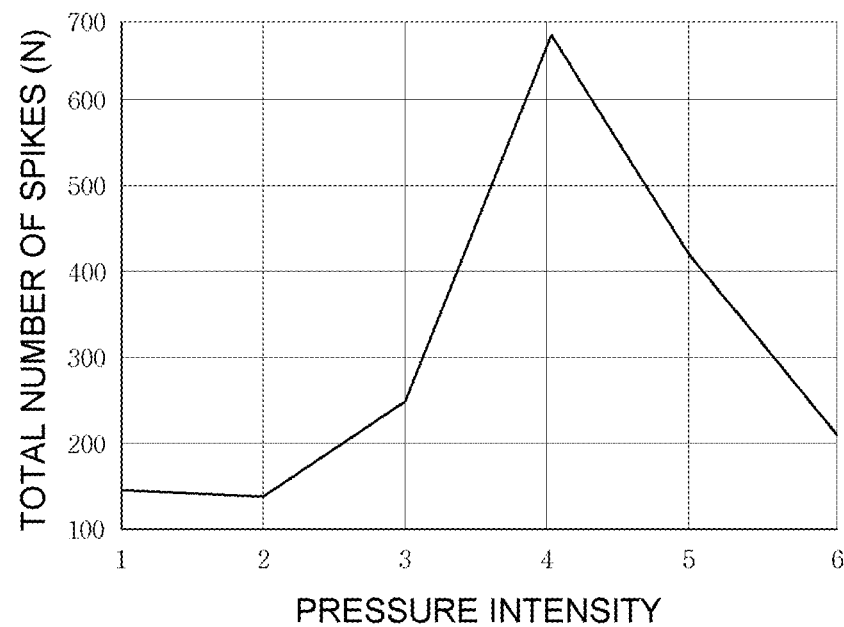
FIG. 3 is a graph showing the total number of spikes according to pressure intensity.
Figure 4A:
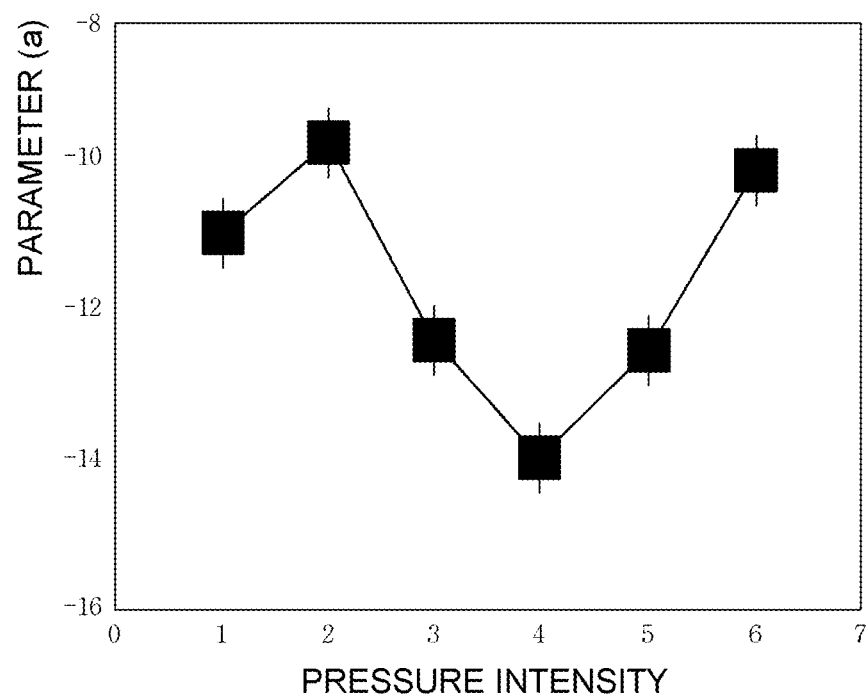
Figure 4B:
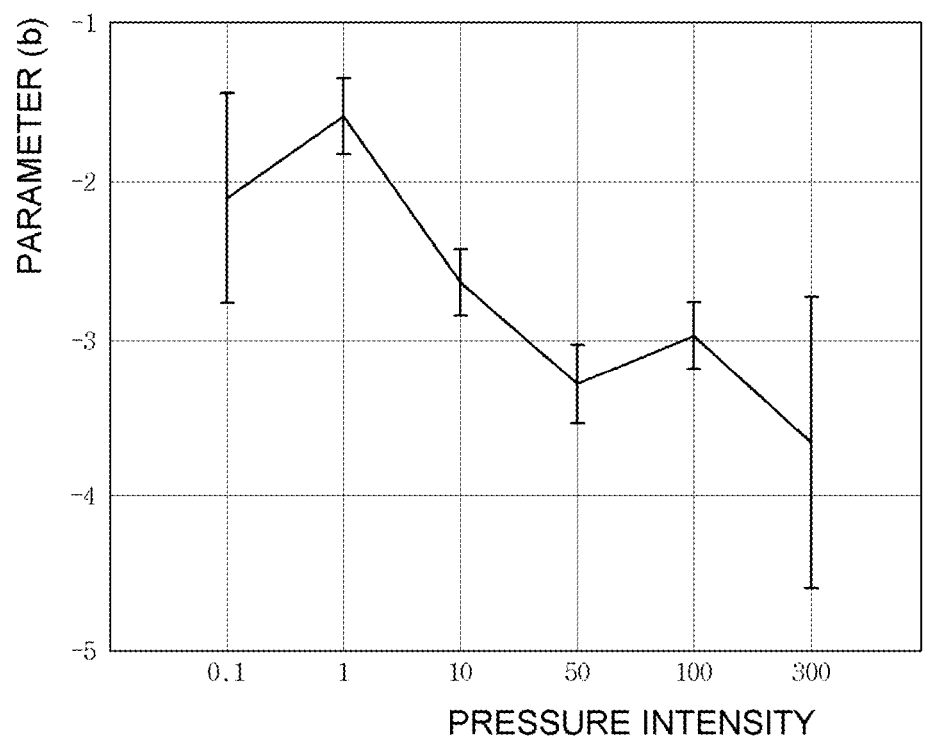
Figure 5:
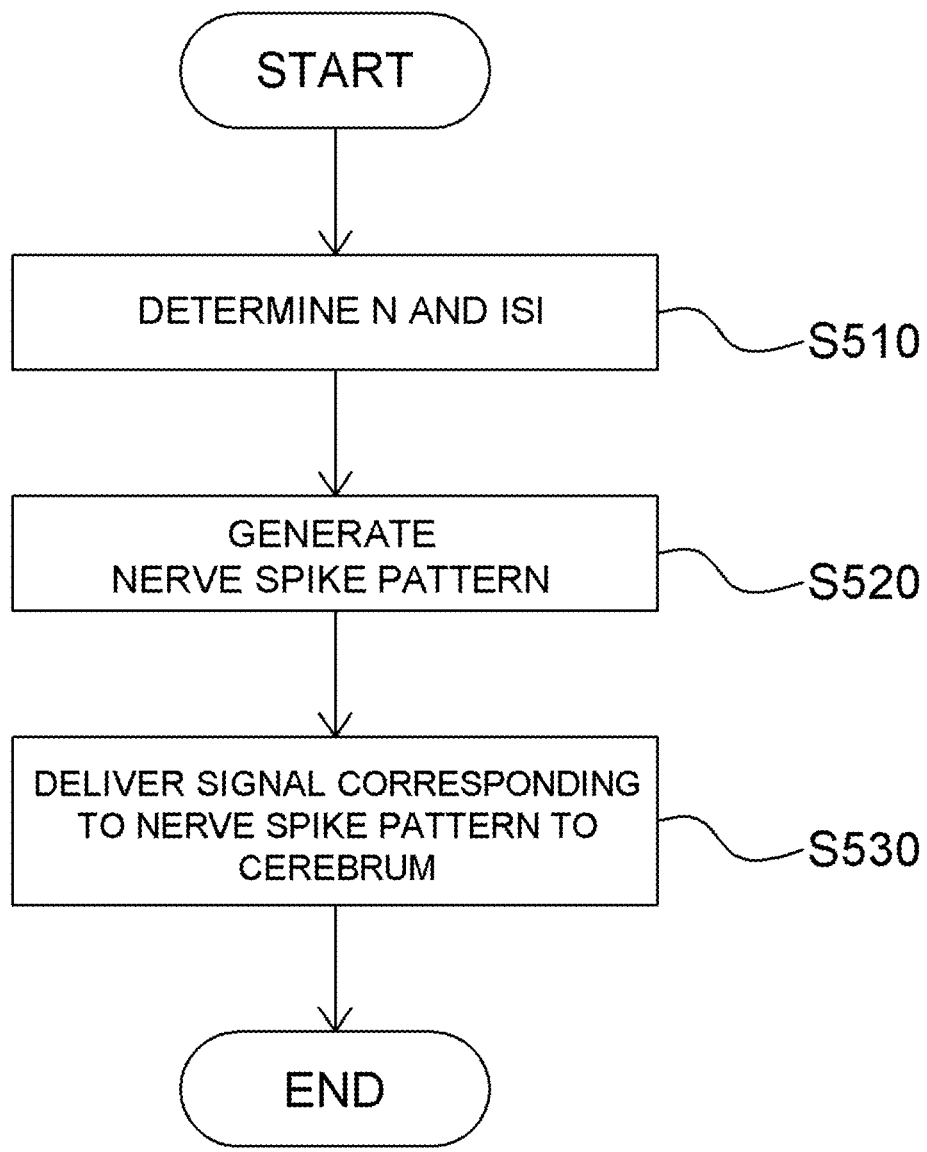
FIG. 5 is a flowchart showing a method of generating a pressure sensation according to an embodiment of the present invention.

FIG. 1 is a flowchart showing a method of modeling a pressure sensation and a method of generating a pressure sensation according to an embodiment of the present invention, FIG. 2 is a flowchart showing a method of modeling a pressure sensation according to an embodiment of the present invention, FIG. 3 is a graph showing the total number of spikes according to pressure intensity, FIGS. 4A to 4C show graphs and tables showing spike model parameters of a generated pressure sensation model according to pressure intensity according to an embodiment of the present invention, and FIG. 5 is a flowchart showing a method of generating a pressure sensation according to an embodiment of the present invention.

This embodiment relates to a method of modeling a nerve spike pattern to model a pressure sensation included in a tactile sensation and a method of generating a pressure sensation included in a tactile sensation by generating a nerve spike pattern using the model. A flowchart of the embodiment is shown in FIG. 1.

Referring to FIG. 2, the method of modeling a pressure sensation according to this embodiment may include stimulating skin by applying pressure to the skin (S210), generating a nerve spike pattern (or a nerve spike train) by sequentially arranging action potential spike time points of a nerve responding to the pressure (S220), measuring the total number N of generated spikes on the basis of the nerve spike pattern (S230), measuring an inter spike interval (ISI) between spike time points of the spikes on the basis of the nerve spike pattern (S240), and functionalizing the measured ISI between the spike time points (S250).

Operation S210 is an operation of stimulating skin by applying a specific pressure to the skin and also is an operation of stimulating skin by applying a certain intensity of pressure to the skin. The initial intensity of the pressure that stimulates the skin is not specified and may be appropriately set depending on a purpose of use and an environment. The period of applying the pressure is not specified and may also be appropriately set depending on the purpose of use and the environment. The skin may be human skin or animal skin.

Operation S220 is an operation of generating a nerve spike pattern by sequentially arranging action potential spike time points of a nerve responding to the pressure. In this case, the nerve responding to the pressure sensation is a slowly adapting (SA) afferent nerve. On the basis of the nerve spike pattern generated in operation S220, a pressure sensation for a specific pressure may be modeled.

Operation S230 is an operation of measuring the total number (hereinafter referred to as "N") of generated spikes from the spike time points shown in the nerve spike pattern. That is, N represents the total number of spikes generated while pressure is being applied. The nerve spike pattern is generated by arranging the spike time points, and thus the total number of generated spikes may be measured on the basis of the nerve spike pattern.

Operation S240 is an operation of calculating an ISI between spike time points on the basis of the nerve spike pattern, that is, an operation of measuring an ISI between spike time points shown in the nerve spike pattern. Operation 250 is an operation of functionalizing the ISI.

The nerve spike pattern of the SA afferent nerve has characteristics in which a large number of spikes are generated within a short time immediately after the pressure is applied and in which the number of spikes is decreased when the pressure is continuously applied. That is, the nerve spike pattern has characteristics in which the degree to which spikes are generated varies over time under pressure.

Thus, the ISI may also vary over time under pressure (time-varying). That is, when the nerve spike pattern of the SA afferent nerve is observed while a certain intensity of pressure is applied to skin, a large number of spikes are generated within a short time immediately after the pressure is applied, and the number of spikes is decreased when the pressure is continuously applied. Thus, the ISI may be increased or decreased over time under pressure.

The change in the ISI with time may be functionalized to a certain function with respect to time. The functionalization method is not specified, and an appropriate method may be selected depending on the purpose of use and the environment.

Preferably, the functionalization may be performed through data fitting using the certain function with respect to time. The ISI is gradually increased when a specific intensity of pressure is maintained. Accordingly, it is preferable that an increasing function be used when data fitting is performed. More preferably, a fifth-order polynomial function defined by the following Equation 1 may be used. In this case, a nerve spike pattern for pressure may be most accurately modeled.

$$y=ax^5+b \quad \text{[Equation 1]}$$

where x indicates time, and y indicates ISI (hereinafter, the coefficients a and b of Equation 1 are referred to as "spike model parameters," and spike model parameters may have values varying depending on pressure intensity).

Operation S250 may include an operation of calculating the coefficients a and b of Equation 1, that is, the spike model parameters according to x and y. That is, the spike model parameters may be determined by performing data fitting on the change in the ISI with time using Equation 1. As a result, it is possible to obtain a correspondence between ISI and time (hereinafter, the correspondence between time and ISI is referred to as "ISI model").

For example, when a pressure with an intensity of 10 mN is applied for 20 seconds, the total number N of spikes generated for 20 seconds is calculated. Also, an ISI between spike time points of the spikes generated for the 20 seconds may be calculated. By performing data fitting on the calculated data using Equation 1, the spike model parameters a and b may be determined, and thus the ISI model may be obtained.

Meanwhile, the functionalization may be performed in the entire time interval or may be performed separately for each of a plurality of time intervals into which the entire time interval is divided. For example, when a pressure is applied for 20 seconds, the functionalization may be performed by setting a time point at which the application of the pressure is started to be 0 sec, performing division into two time intervals, that is, 1) a time interval from 0 sec to 0.8 sec and 2) a time interval from 0.8 sec to 20 sec, and performing data fitting for each time interval. The method of performing time interval division is not specified, and an appropriate method may be selected depending on the purpose of use and the environment.

However, operations S240 and S250 may be performed before or simultaneously with operation S230. That is, in the above example, the ISI model may be obtained before or at the same time the total number N of spikes may be calculated.

Operations S210 to S250 are performed on a specific pressure, and then operations S210 to S250 are repeatedly performed on other pressures, that is, after the intensity of the pressure is changed. By repeating this process, ISI models corresponding to various intensities of pressure may be obtained.

Also, by repeatedly performing operation S230 on the changed pressure, a correspondence between pressure intensity and N may be obtained (hereinafter, the correspondence between pressure intensity and N is referred to as "N model").

FIG. 3 is a graph showing the correspondence between pressure intensity and N. Referring to FIG. 3, it can be seen that N is maximized at a specific intensity of pressure and is decreased as the pressure is increased over the specific intensity.

Such a tendency is reflected in the spike model parameter a. That is, as N is increased, the ISI becomes smaller and the spike is generated for a longer time compared to when N is small. Thus, the spike model parameter a is decreased. FIG. 4A shows the spike model parameter a of an SA1 afferent nerve according to pressure intensity. Referring to an SA1 item of FIG. 4C, it can be seen that the value of the spike model parameter tends to be decreased and then increased.

FIG. 4B shows the spike model parameter b of the SA1 afferent nerve according to pressure intensity. It can be seen that the value of the spike model parameter tends to be increased for a certain interval and then decreased. Also, an SA2 item of FIG. 4C indicates the spike model parameter a of an SA2 afferent nerve according to pressure intensity. In the SA2 afferent nerve, N tends to be increased as the pressure is increased. Thus, according to the above-described principle, the spike model parameter a tends to be gradually decreased.

Meanwhile, by using the N model and the ISI model obtained in the above method, a nerve spike pattern corresponding to a pressure with a desired specific intensity may be generated, and thus a virtual tactile sensation may be generated. The method will be described in detail below with reference to FIG. 1 and FIG. 5.

Referring to FIG. 5, the method of generating a pressure sensation according to this embodiment may include determining N and ISI of a nerve spike pattern to be generated using a pressure sensation model (S510), generating a nerve spike pattern on the basis of the determined N and ISI (S520), and delivering a signal corresponding to the generated nerve spike pattern to a cerebrum.

Operation S510 is an operation of determining N and ISI of a nerve spike pattern to be generated using a generated pressure sensation model. That is, N and ISI of the nerve spike pattern corresponding to a virtual pressure sensation with an intensity to be generated may be determined using the pressure sensation model.

First, the total number of spikes of the nerve spike pattern to be generated using the N model may be determined and is equal to N, which is for a specific pressure intensity. Referring back to FIG. 3, it can be seen that since there is a correspondence between the pressure intensity and N, the total number of spikes of the nerve spike pattern to be generated using the N model may be determined when the pressure intensity is known.

Also, an ISI between spike time points of the nerve spike pattern corresponding to the specific pressure intensity may be determined using the ISI model and may be extracted from an ISI model for the specific pressure intensity. Referring back to FIGS. 4A to 4C, it can be seen that since the spike model parameters a and b have a correspondence with the pressure intensity, an ISI model corresponding to a specific intensity of pressure may be determined, and an ISI between spike time points of a nerve spike pattern may be extracted using the determined ISI model.

In this case, the method of extracting an ISI between spike time points to be shown in a nerve spike pattern from an ISI model is not specified, and an appropriate method may be used depending on the purpose of use and the environment.

For example, first, a time interval value corresponding to a specific time is extracted from a tactile sensation model at the specific time and is set as a mean. That is, y (the value of ISI) corresponding to x (the value of time) is set as a mean. Also, a predetermined constant value is set as a variance. The method of setting a variance and the value of the variance are not specified and may be appropriately set depending on the purpose of use and the environment.

Also, a probability distribution defined using the set mean and variance is obtained. Preferably, the probability distribution may be Poisson distribution or Gamma distribution. Also, a random value may be extracted using the probability distribution, and the extracted value may be determined as an ISI. Preferably, the value may be extracted using the Gamma distribution. In this case, it is possible to more accurately generate a nerve spike pattern.

Operation S520 is an operation of generating a nerve spike pattern using the determined N and ISI. Since the ISI value indicates an inter spike interval between spike time points, the nerve spike pattern may be generated by setting an initial spike time point and then placing (arranging) a predetermined number of spike time points at the determined intervals. That is, the nerve spike pattern may be generated by arranging a number of spike time points equal to the determined total number N of spikes in a line to be spaced the determined ISI apart from one another.

Meanwhile, the nerve spike pattern may be generated after the ISI between the spike time points of the nerve spike pattern corresponding to a specific intensity of pressure is determined on the basis of the ISI model first and then the total number of spikes of the nerve spike pattern to be generated using the N model is determined.

Operation S530 is an operation of generating a signal corresponding to the generated nerve spike pattern and delivering the generated signal to a cerebrum. The signal generation method and the signal delivery method are not specified, and appropriate methods may be used depending on the purpose of use and the environment.

An experimental example according to an embodiment of the present invention will be described below with reference to FIG. 6. In this experimental example, a pressure was applied to an animal's sole skin to generate a nerve spike pattern and model a pressure sensation. Also, a nerve spike pattern was generated using the model to verify the accuracy thereof. A description of contents overlapping those described above will be omitted below.

Figure 6:
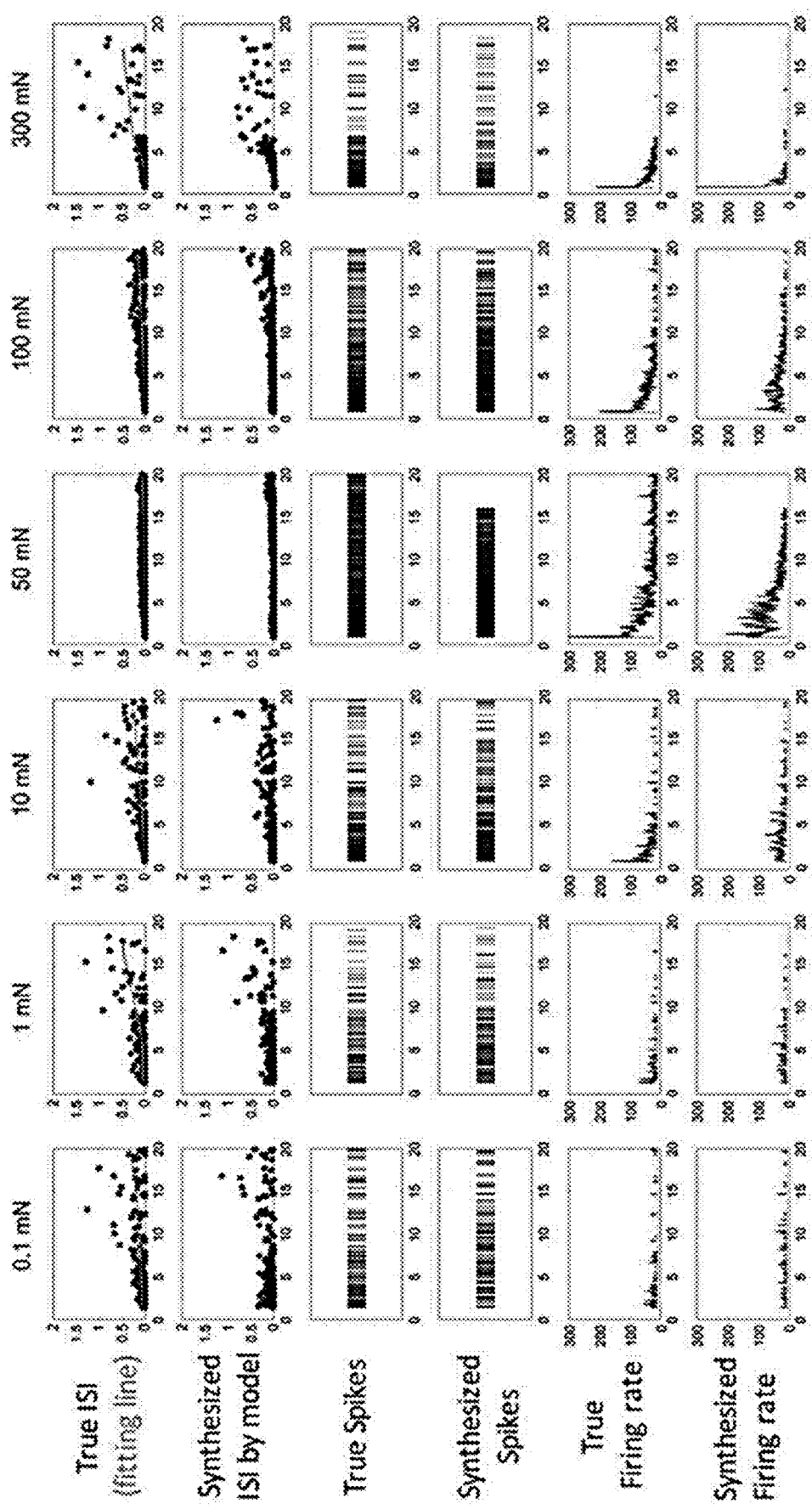
FIG. 6 is a diagram showing an experimental example of modeling a pressure sensation, generating a nerve spike pattern on the basis of the model, and confirming the accuracy of the nerve spike pattern through comparison according to an embodiment of the present invention.

[Experimental Example 1] Experiment of Modeling Pressure Sensation and Generating Nerve Spike Pattern Using Model FIG. 6 is a diagram showing an experimental example of modeling a pressure sensation, generating a nerve spike pattern on the basis of the model, and checking the accuracy of the nerve spike pattern through comparison. The experiment was performed with different pressures for each column.

Referring to FIG. 6, a first row shows a change in ISI with time when each pressure is maintained. For example, the drawing shown at the rightmost side shows a change in ISI with time when the highest pressure (300 mN) is maintained.

Data fitting may be performed on data regarding the change in ISI with time using Equation 1. In the first row, a red line of each picture indicates a data fitting result (fitting line).

A second row shows a result obtained by determining an ISI value to be used when a nerve spike pattern corresponding to a specific pressure is generated using the data fitting result. In detail, in the fitting line, y (the value of ISI) corresponding to x (the value of time) is set as a mean, and a constant value is set as a variance. Also, a value may be extracted using the Gamma distribution, and the extracted value may be determined as an ISI value to be used when the nerve spike pattern is generated.

A third row shows an actual nerve spike pattern generated while pressure is applied, and a fourth row shows a nerve spike pattern generated using a nerve spike pattern model.

Meanwhile, a spike rate is defined as the number of spikes per unit time and may be calculated by counting the number of times a spike is generated during a specific time interval. When it is assumed that the pressure sensation is accurately modeled, a spike rate calculated on the basis of a nerve spike pattern generated from the model may have a similar value or form to the spike rate calculated from the actual nerve spike pattern.

A fifth row indicates a result of calculating the spike rate from the actual nerve spike pattern, and a sixth row indicates a result of calculating the spike rate from the nerve spike pattern generated using the extracted ISI value. It can be seen that the above spike rates have similar forms. According to the present invention, it can be seen that it is possible to very accurately generate a nerve spike pattern corresponding to a specific pressure using a pressure sensation model.

A method of modeling a vibration sensation using a nerve spike pattern, a vibration sensation model, and a method of generating a vibration sensation according to another embodiment of the present invention will be described below.

Figure 7:
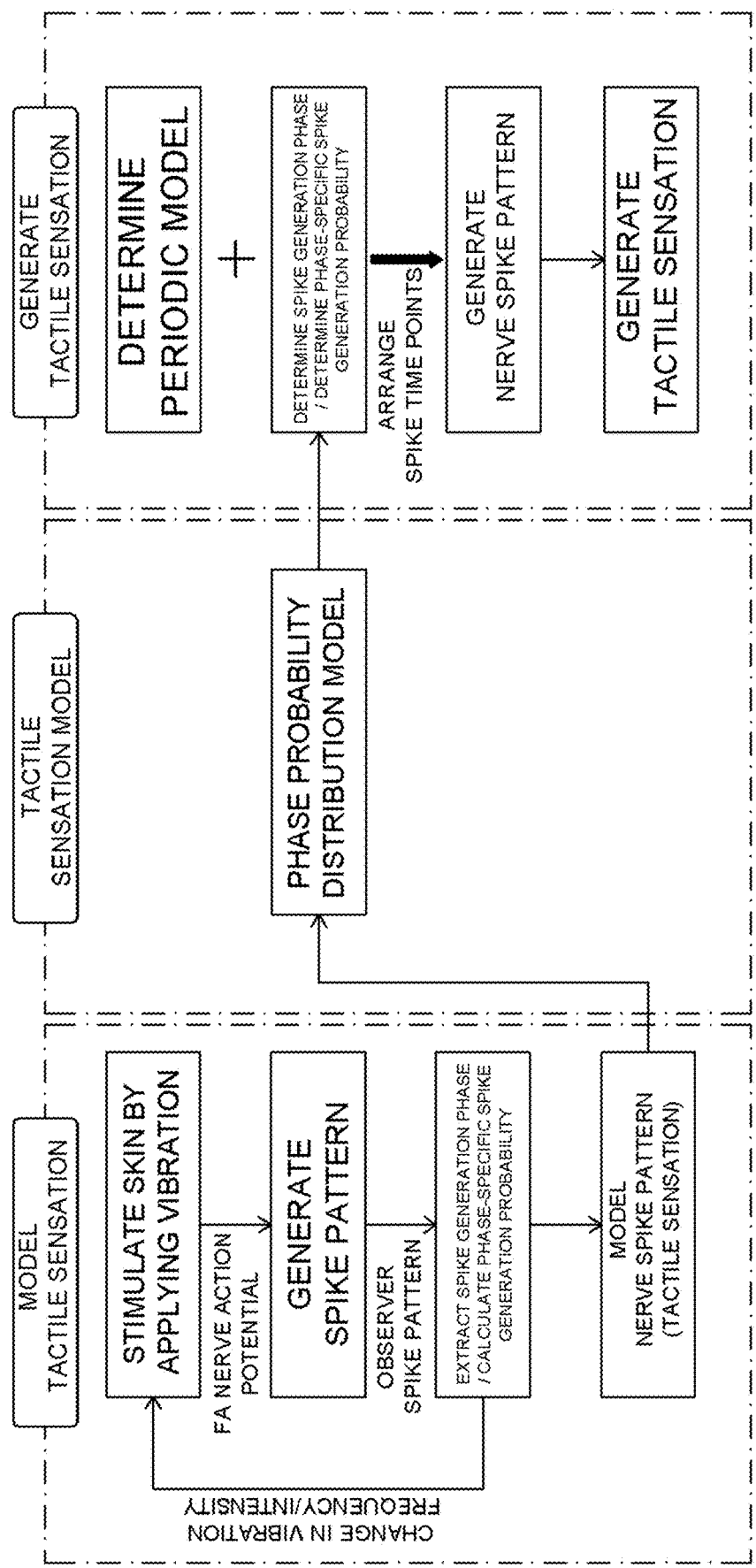
FIG. 7 is a diagram showing a method of modeling a vibration sensation and a method of generating a vibration sensation according to another embodiment of the present invention.
Figure 8:
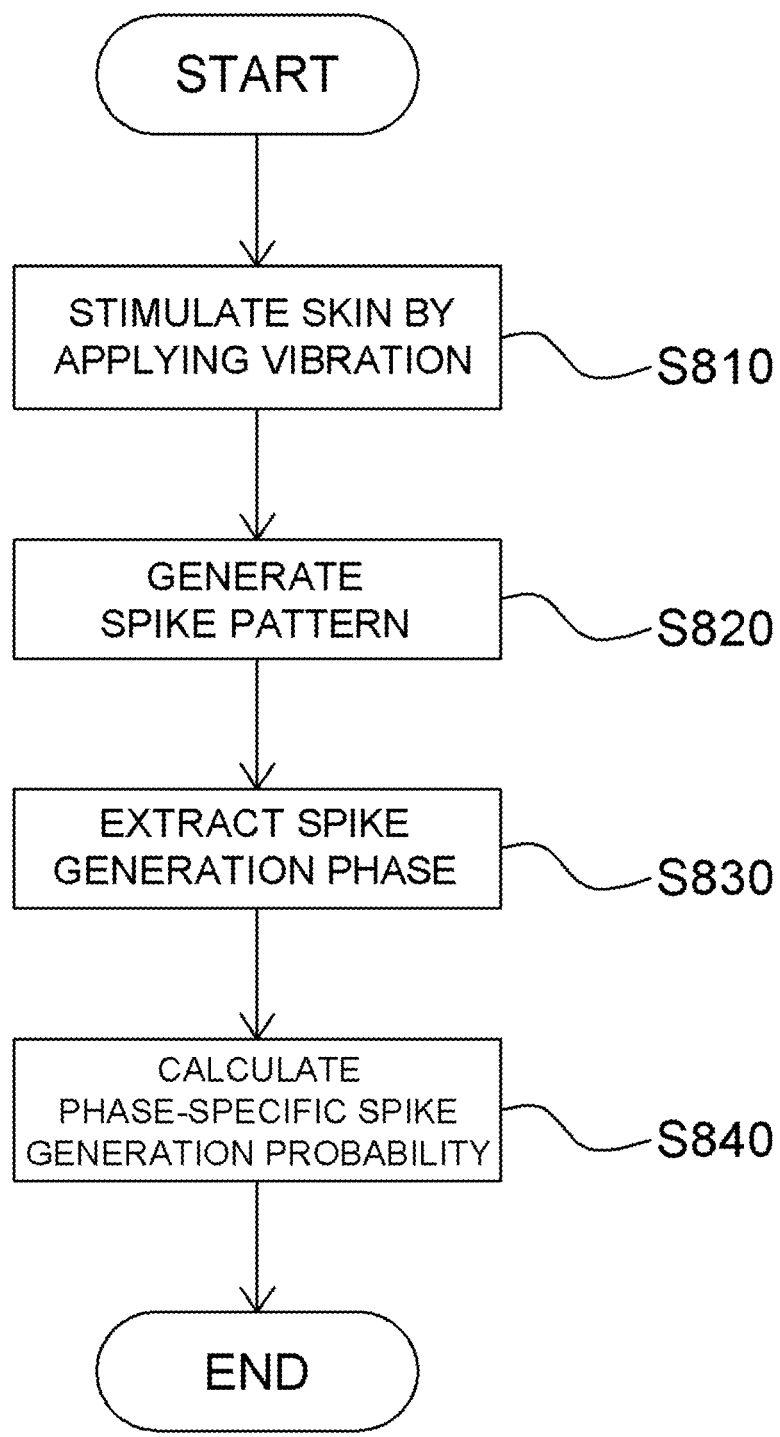
FIG. 8 is a flowchart showing a method of modeling a vibration sensation according to another embodiment of the present invention.
Figure 9B:
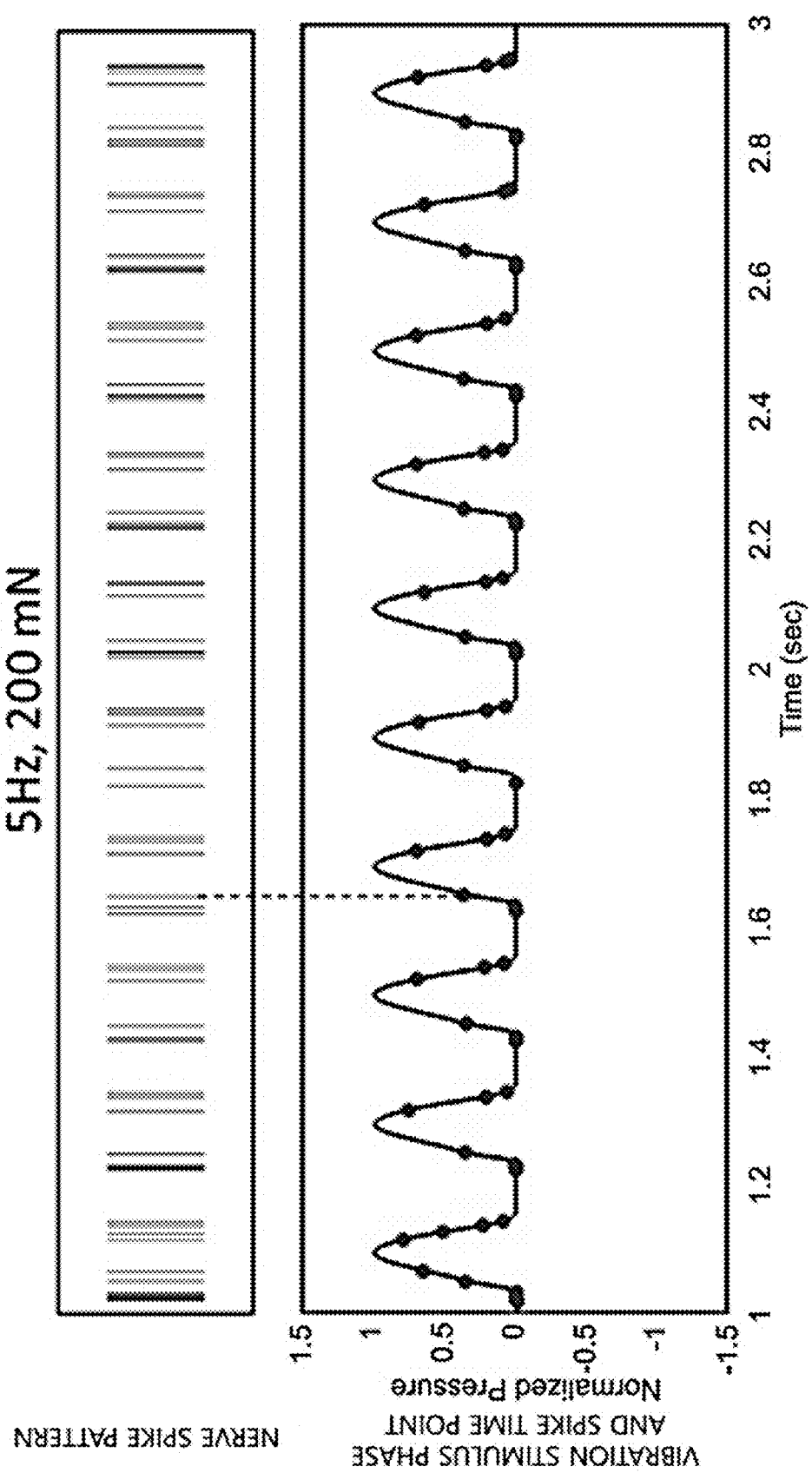
Figure 10B:
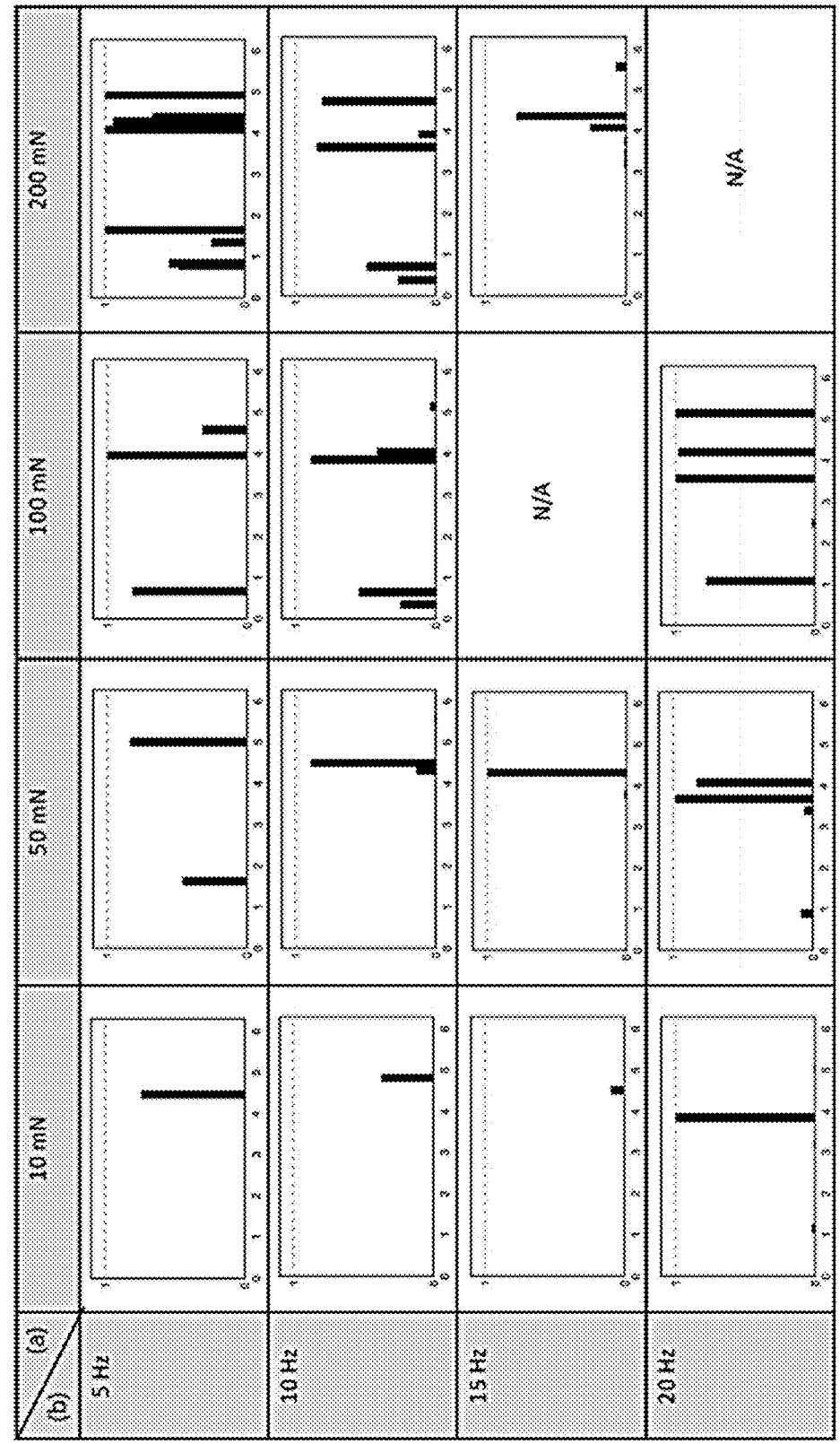

FIG. 7 is a diagram showing a method of modeling a vibration sensation and a method of generating a vibration sensation according to another embodiment of the present invention, FIG. 8 is a flowchart showing a method of modeling a vibration sensation according to another embodiment of the present invention, FIGS. 9A and 9B are diagrams showing an example of a nerve spike pattern for a vibration stimulus, FIGS. 10A and 10B are diagrams showing a phase of a vibration stimulus where a spike is generated and a phase-specific spike generation probability, and FIG. 11 is a flowchart showing a method of generating a vibration sensation according to another embodiment of the present invention.

This embodiment relates to a method of modeling a nerve spike pattern to model a vibration sensation included in a tactile sensation and a method of generating a vibration sensation included in a tactile sensation by generating a nerve spike pattern using the model. A flowchart of the embodiment is shown in FIG. 7.

Referring to FIG. 8, the method of modeling a vibration sensation according to this embodiment may include stimulating skin by applying a vibration stimulus to the skin (S810), generating a nerve spike pattern (or a nerve spike train) by sequentially arranging action potential spike time points of a nerve responding to the vibration stimulus (S820), measuring a phase of the vibration stimulus where a spike is generated from the nerve spike pattern (S830), and calculating a spike generation probability for the measured phase (S840).

Operation S810 is an operation of stimulating skin by applying a specific vibration stimulus to the skin and also is an operation of stimulating skin by applying a predetermined vibration stimulus to the skin during a predetermined time period. The vibration stimulus may be a stimulus with a predetermined frequency and amplitude and may be in the form of a periodic function. For example, the vibration stimulus may vibrate in the form of a sine wave and may repeatedly increase and decrease in intensity of the stimulus. The initial values of the frequency and amplitude are not specified and may be appropriately set depending on the purpose of use and the environment. The period of applying the vibration stimulus is not specified and may also be appropriately set depending on the purpose of use and the environment. The skin may be human skin or animal skin.

Operation S820 is an operation of generating a nerve spike pattern by sequentially arranging action potential spike time points of a nerve responding to the vibration stimulus. In this case, the nerve responding to the vibration stimulus is a fast adapting (FA) afferent nerve. A vibration sensation for a specific vibration stimulus may be modeled on the basis of the nerve spike pattern generated in operation S820.

Meanwhile, FIG. 9A shows a nerve spike pattern, a vibration stimulus phase, and a spike time point of a vibration stimulus with a frequency of 5 Hz and an amplitude of 50 mN.

Referring to FIG. 9A, it can be seen that a spike was periodically generated in the phase of an area depicted by a square. Meanwhile, it can also be seen that a spike was also generated in the phase of an area depicted by a square but no spike was generated in the phase of an area depicted by a square indicating the same phase. This is because a spike is generated probabilistically for each phase of the vibration stimulus. That is, the nerve spike pattern of the FA afferent nerve has characteristics in which a spike is generated in a specific phase and also probabilistically.

Meanwhile, FIG. 9B shows a nerve spike pattern, a vibration stimulus phase, and a spike time point of a vibration stimulus with a frequency of 5 Hz and an amplitude of 200 mN.

Referring to FIG. 9B, it can be seen that the phase where the spike is generated changes along with variation in the amplitude of the vibration stimulus. That is, it can be seen that the phase where the spike is generated and the probability that the spike will be generated in the phase vary along with the amplitude of the vibration stimulus. This is true even when the vibration stimulus varies in frequency.

Accordingly, in order to model the vibration sensation caused by the vibration stimulus, the phase where the spike is generated should be measured on the basis of the nerve spike pattern, and the probability that the spike will be generated in the measured phase should be calculated. This is performed in operations S830 and S840.

Operation S830 is an operation of measuring the phase where the spike is generated on the basis of the nerve spike pattern, and operation S840 is an operation of calculating the probability that the spike will be generated in the measured phase.

The method of measuring the phase where the spike is generated on the basis of the nerve spike pattern is not specified, and an appropriate method may be selected depending on the purpose of use and the environment. For example, the measurement may be performed by extracting the phase of the vibration stimulus where the spike is generated using Hilbert transform.

Meanwhile, the phase may have a value ranging from 0 to 2n. Thus, the range may be equally divided into a plurality of phase intervals having a predetermined length (size), and then a phase-interval-specific spike generation probability may be calculated. That is, the probability that the measured phase will belong to any one of the plurality of phase intervals may be calculated.

For example, the phase-interval-specific spike generation probability may be calculated by equally dividing the range from 0 to $2\pi$ into 40 phase intervals, checking to which phase interval measured phases belong, and counting the number of phases belonging to each interval.

When a time at which the vibration stimulus is applied and the frequency of the vibration stimulus are known, the probability that a spike is generated for each interval may be calculated. For example, it is assumed that a vibration stimulus having a frequency of 5 Hz is applied for eleven seconds. In this case, the vibration stimulus vibrates five times per second and thus is applied a total of 55 times. In this case, when twenty spikes are generated in a specific phase interval, the probability where the spike is generated in the corresponding phase interval is equal to 4/11 (=20/55).

Operations S810 to S840 are performed on a specific vibration stimulus, and then operations S810 to S840 are repeatedly performed under other vibration stimuli, that is, after the frequency and/or amplitude of the vibration stimulus are changed. By repeating this process for vibration stimuli with various frequencies and amplitudes, data regarding phases of vibration stimuli where the spike is generated and data regarding probabilities that the spike will be generated in the corresponding phases may be extracted (hereinafter, the extracted data is referred to as a "phase probability distribution model").

FIGS. 10A and 10B are diagrams showing a phase of a vibration stimulus where a spike is generated and a phase-specific spike generation probability, and correspond to examples of the phase probability distribution model. The phase probability distribution model is not only written in a table, but may be made in a form appropriate for the purpose of use and the environment.

Referring to FIG. 10, it can be seen that the number of spikes tends to increase as the frequency of the vibration stimulus increases and as the amplitude of the vibration stimulus increases. Also, it can be seen that in particular, that is, when a vibration stimulus with a frequency of 15 Hz and an amplitude of 100 mN is applied and when a vibration stimulus with a frequency of 20 Hz and an amplitude of 200 mN is applied, the FA afferent nerve does not respond (N/A).

Meanwhile, by using the phase probability distribution model obtained by the above method, that is, the vibration sensation model, a nerve spike pattern corresponding to a vibration stimulus with a desired specific frequency and amplitude may be generated, and a virtual tactile sensation may be generated through the nerve spike pattern. The method will be described in detail below with reference to FIG. 7 and FIG. 11.

Referring to FIG. 11, the method of generating a vibration sensation according to this embodiment may include determining a periodic function corresponding to a vibration stimulus (S1110), determining a spike generation phase using a vibration sensation model (S1120), determining a spike-generation-phase-specific spike generation probability using the vibration sensation model (S1130), generating a nerve spike pattern on the basis of the determined spike generation phase and spike generation probability (S1140), and delivering a signal corresponding to the generated nerve spike pattern to a cerebrum (S1150).

Operation S1110 is an operation of determining a periodic function corresponding to a vibration stimulus. A periodic function corresponding to a vibration stimulus with a desired specific frequency and amplitude is determined. That is, a periodic model (corresponding to a black line of FIG. 9) corresponding to a vibration stimulus with a desired specific frequency and amplitude is determined. The periodic model may be normalized to a desired specific frequency. For example, the periodic model may be set to a sine wave with a predetermined frequency and amplitude.

Operation S1120 is an operation of determining a spike generation phase using a vibration sensation model. Phases corresponding to spikes of the nerve spike pattern to be generated from a tactile sensation model are determined. That is, phases where a spike will be generated when a vibration stimulus is actually applied are predicted using the phase probability distribution model and are determined as the phases corresponding to the spikes of the nerve spike pattern to be generated.

Operation S1130 is an operation of determining a spike-generation-phase-specific spike generation probability using the vibration sensation model. Referring to FIG. 9A again, the nerve spike pattern of the FA afferent nerve has characteristics in which a spike is generated in a specific phase and also probabilistically. Accordingly, only when the spike generation probability for each of the determined spike generation phases should also be determined, the nerve spike pattern may be generated.

Operation S1140 is an operation of generating the nerve spike pattern on the basis of the determined spike generation phase and spike generation probability. A nerve spike pattern corresponding to a vibration stimulus with a specific frequency and amplitude is generated using the determined periodic model, the phase of the periodic function where the spike is predicted to be generated, and the spike generation probability of the extracted phase. That is, the nerve spike pattern may be generated by arranging spike time points to correspond to the phase extracted using the extracted spike generation probability.

In this case, the method of arranging the spike time points is not specified, and an appropriate method may be used depending on the purpose of use and the environment. For example, the probability distribution may be used. Preferably, the Poisson distribution may be used.

For example, a process of generating a nerve spike pattern corresponding to a vibration stimulus with a frequency of 5 Hz and an amplitude of 50 mN will be described.

First, a sine function with a frequency of 5 Hz and an amplitude of 50 mN is set. Also, referring to FIG. 10 again, it can be seen that in the case of a vibration stimulus with a frequency of 5 Hz and an amplitude of 50 mN, a spike is generated with 46% probability at a phase value of 1.62 and a spike is generated with 84% probability at a phase value of 5.00. By arranging the spike time points using this data, the nerve spike pattern may be generated.

Operation S1150 is an operation of generating a signal corresponding to the generated nerve spike pattern and delivering the generated signal to a cerebrum. The signal delivery method is not specified, and an appropriate method may be used depending on the purpose of use and the environment.

An experimental example according to another embodiment of the present invention will be described below with reference to FIG. 11. In this experimental example, a vibration stimulus was applied to an animal's sole skin to generate a nerve spike pattern and model a vibration sensation. Also, a nerve spike pattern was generated using the model to verify the accuracy thereof. A description of contents overlapping those described above will be omitted below.

[Experimental Example 2] Experiment of Modeling Vibration Sensation and Generating Nerve Spike Pattern Using Model FIG. 12 is a diagram showing an experimental example for modeling a vibration sensation, generating a nerve spike pattern on the basis of the model, and confirming the accuracy of the nerve spike pattern through comparison. An actual nerve spike pattern obtained by fixing the frequency of the vibration stimulus to 5 Hz and changing only the intensity of the vibration stimulus to 50 mN or 200 mN (a true spike) and a nerve spike pattern generated using the nerve spike pattern model (a simulated spike by model) are shown.

When the vibration sensation is accurately modeled, the nerve spike pattern generated from the model may have a similar form to the actual nerve spike pattern.

Figure 12A:
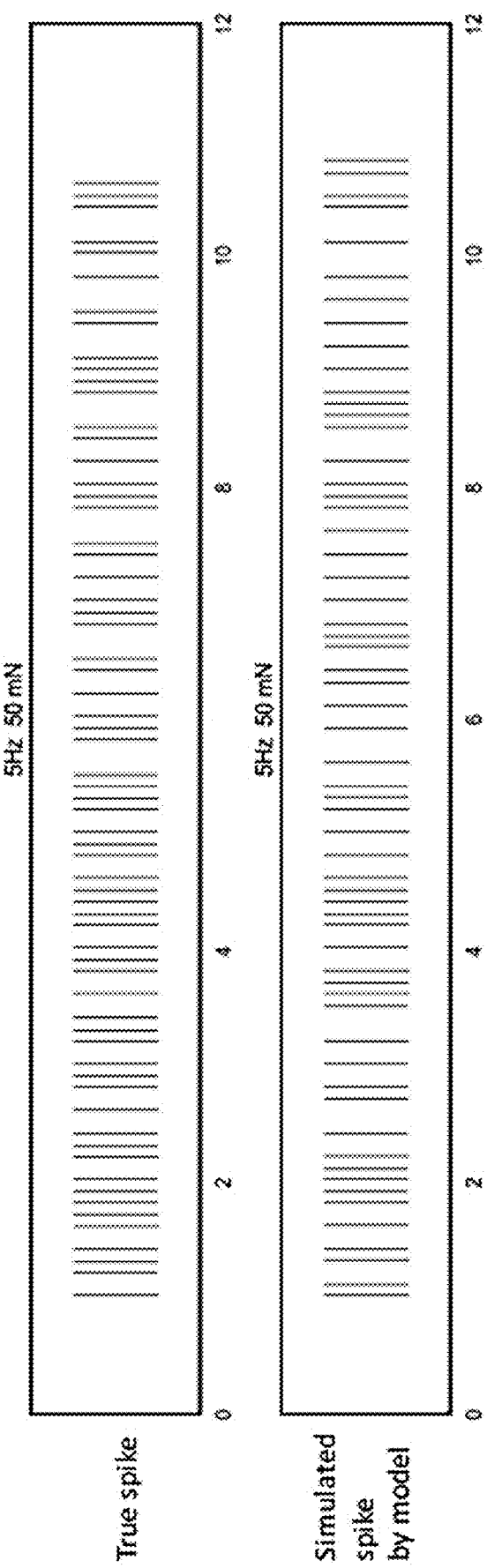
FIGS. 12A and 12B are diagrams showing an experimental example of modeling a vibration sensation, generating a nerve spike pattern on the basis of the model, and confirming the accuracy of the nerve spike pattern through comparison according to another embodiment of the present invention.
Figure 12B:
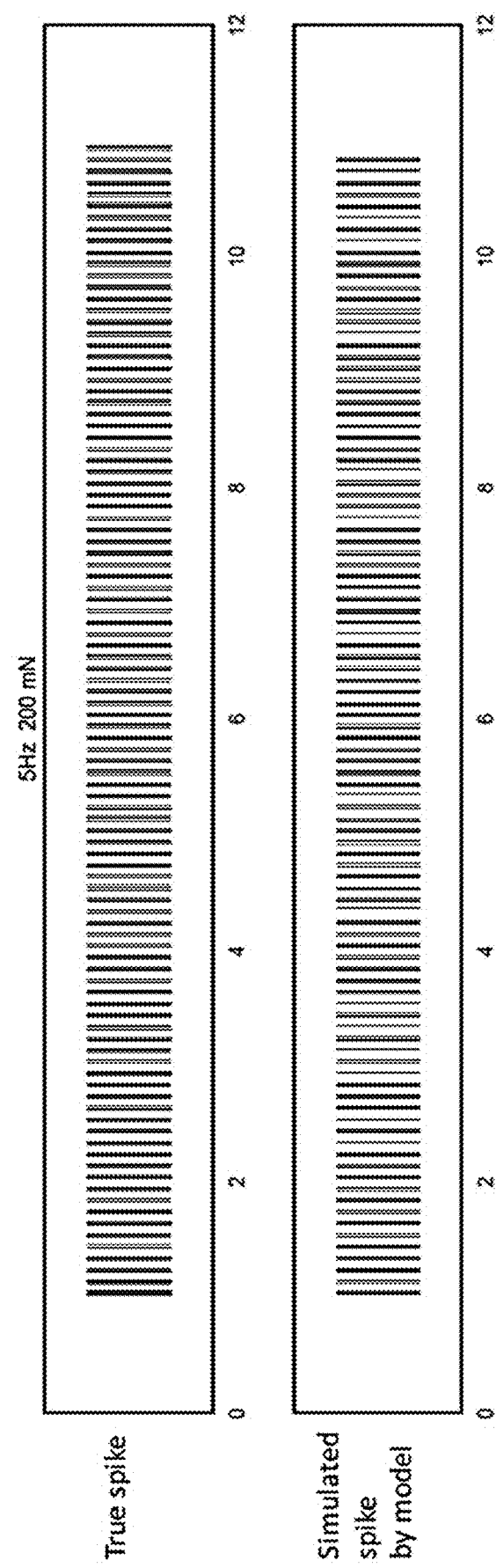

Referring to FIGS. 12A and 12B, it can be seen that the actual nerve spike pattern and the nerve spike pattern generated using the vibration sensation model have very similar forms. That is, according to the present invention, it can be seen that a nerve spike pattern corresponding to a predetermined vibration may be very accurately generated using the vibration sensation model so that it is possible to accurately implement a virtual vibration sensation.

According to the present invention described above, by checking how tactile sensation information is reflected in a nerve spike pattern, it is possible to provide a method capable of modeling various tactile sensations using the nerve spike pattern.

Also, by allowing a tactile sensation model having information regarding various tactile sensations to be modeled, it is possible to provide source technology capable of creating a tactile sensation map for the various tactile sensations.

In addition, by allowing a nerve spike pattern corresponding to a tactile sensation desired to be generated on the basis of a tactile sensation model, it is possible to provide a method capable of implementing the tactile sensation in virtual reality or the like.

The above description is merely illustrative of the technical sprit of the present invention, and it will be apparent to those skilled in the art that various modifications and variations can be made therein without departing from the essential characteristics of the invention.

Accordingly, the embodiments disclosed herein are intended not to limit but to describe the technical sprit of the present invention, and the scope of the present invention is not limited by the embodiments.

The scope of the present invention should be interpreted by the appended claims, and all the technical sprits in the equivalent range should be understood as being embraced by the claims of the present invention.

The invention claimed is:

1. A method of modeling a tactile sensation using a nerve spike pattern, the method comprising:
generating a nerve spike pattern by sequentially arranging action potential spike time points of a nerve responding to a specific pressure; and
modeling a pressure sensation for the pressure on the basis of the generated nerve spike pattern.

2. The method of claim 1, wherein the modeling comprises:
measuring the total number N of generated spikes and inter spike intervals (ISIs) between spike time points of the spikes on the basis of the generated nerve spike pattern; and
modeling the pressure sensation through the measured total number of spikes and the measured ISIs between the spike time points.

3. The method of claim 2, wherein,
the measured ISIs are time-varying, and
the measuring comprises functionalizing a change in the ISIs with time using an ISI measured at a specific time.

4. The method of claim 3, wherein,
a function obtained through the functionalizing is $$y=ax^5+b$$

where x indicates time and y indicates ISI between spike time points, and
the functionalizing comprises computing a and b of the function according to x and y.

5. The method of claim 3, wherein the functionalizing is performed separately for a plurality of time intervals obtained through division.

6. The method of claim 4, wherein the computing is performed separately for a plurality of time intervals obtained through division.

7. The method of claim 1, wherein after the modeling of the pressure sensation for the specific pressure, the generating and the modeling are repeatedly performed under pressures different from the specific pressure.

8. A method of modeling a tactile sensation using a nerve spike pattern, the method comprising:
generating a nerve spike pattern by sequentially arranging action potential spike time points of a nerve responding to a specific vibration stimulus; and
modeling a vibration sensation for the vibration stimulus on the basis of the generated nerve spike pattern.

9. The method of claim 8, wherein the modeling comprises:
measuring phases of the vibration stimulus where spikes are generated in the generated nerve spike pattern; and
calculating spike generation probabilities for the measured phases.

10. The method of claim 9, wherein the measuring comprises measuring the phases through Hilbert transform.

11. The method of claim 9, wherein the calculating comprises:
equally dividing a phase interval ranging from 0 to $2\pi$ into a plurality of phase intervals; and
calculating the probability that each of the measured phases will belong to any one of the plurality of phase intervals.

12. The method of claim 11, wherein the calculating comprises counting the number of phases belonging to each of the plurality of phase intervals to calculate a spike generation probability for each of the plurality of phase intervals.

13. The method of claim 8, wherein after the modeling of the vibration sensation for the specific vibration stimulus, the generating and the modeling are repeatedly performed for vibration stimuli different from the specific vibration stimulus.

14. A tactile sensation model that is obtained through modeling by the method of modeling a tactile sensation using a nerve spike pattern of claim 1.

15. A tactile sensation model that is obtained through modeling by a method of modeling a tactile sensation using a nerve spike pattern of claim 8.

16. A method of generating a tactile sensation using a nerve spike pattern, the method comprising generating a nerve spike pattern corresponding to a specific pressure sensation in a tactile sensation model obtained through modeling by a method of claim 1.

17. The method of claim 16, further comprising delivering a signal corresponding to the generated nerve spike pattern to a cerebrum.

18. The method of claim 16, wherein the generating comprises:
determining the total number of spikes of the nerve spike pattern and inter spike intervals (ISIs) between spike time points on the basis of the tactile sensation model; and
arranging a number of spikes equal to the determined total number of spikes to be spaced the determined ISI apart from one another.

19. The method of claim 18, wherein,
in the determining, the ISIs are determined by a probability distribution having a preset mean and variance, and
the mean is a time interval value corresponding to a specific time in the tactile sensation model.

20. The method of claim 19, wherein the probability distribution is Poisson distribution or Gamma distribution.

21. A method of generating a tactile sensation using a nerve spike pattern, the method comprising generating a nerve spike pattern corresponding to a specific vibration sensation in a tactile sensation model obtained through modeling by a method of claim 8.

22. The method of claim 21, further comprising delivering a signal corresponding to the generated nerve spike pattern to a cerebrum.

23. The method of claim 21, wherein the generating comprises:
determining a periodic function corresponding to the specific vibration sensation; and
generating the nerve spike pattern on the basis of the determined periodic function and the tactile sensation model.

24. The method of claim 23, wherein the generating comprises:
determining phases of the periodic function corresponding to spikes of the nerve spike pattern on the basis of the tactile sensation model;
determining spike generation probabilities for the determined phases on the basis of the tactile sensation model; and
generating the nerve spike pattern on the basis of the determined phases and the determined spike generation probabilities.

25. The method of claim 24, wherein the generating comprises arranging the spikes according to the spike generation probabilities determined to correspond to the determined phases.

* * * * *